(12) United States Patent
Burns, IV et al.

(10) Patent No.: US 11,089,676 B2
(45) Date of Patent: Aug. 10, 2021

(54) MULTI-LAYERED FABRICATION PROCESSING

(71) Applicant: THE CHARLES STARK DRAPER LABORATORY, INC., Cambridge, MA (US)

(72) Inventors: John R. Burns, IV, Boston, MA (US); Jesse J. Wheeler, Revere, MA (US); Andrew Czarnecki, Quincy, MA (US); Carlos A. Segura, Ipswich, MA (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 233 days.

(21) Appl. No.: 16/108,010

(22) Filed: Aug. 21, 2018

(65) Prior Publication Data
US 2019/0059151 A1    Feb. 21, 2019

Related U.S. Application Data

(60) Provisional application No. 62/548,310, filed on Aug. 21, 2017.

(51) Int. Cl.
*H05K 1/02* (2006.01)
*H05K 3/00* (2006.01)
(Continued)

(52) U.S. Cl.
CPC .......... *H05K 1/028* (2013.01); *A61N 1/0404* (2013.01); *A61N 1/0472* (2013.01); *A61N 1/05* (2013.01);
(Continued)

(58) Field of Classification Search
CPC .... H05K 1/028; H05K 1/0393; H05K 3/4635; H05K 3/4007; H05K 1/0218;
(Continued)

(56) References Cited

U.S. PATENT DOCUMENTS

| 7,937,153 B2 | 5/2011 | Zhou et al. |
| 2006/0270942 A1* | 11/2006 | McAdams ............. A61B 5/445 600/547 |

(Continued)

FOREIGN PATENT DOCUMENTS

| EP | 1968360 A1 | 9/2008 |
| EP | 2725881 B1 | 6/2015 |

OTHER PUBLICATIONS

Invitation to Pay Additional Fees in Application No. PCT/US2018/047362 dated Dec. 18, 2018.
(Continued)

*Primary Examiner* — Amanda K Hulbert
*Assistant Examiner* — Philip C Edwards
(74) *Attorney, Agent, or Firm* — Lando & Anastasi, LLP

(57) ABSTRACT

A multi-layered electronic device including two or more stacked metal conducting layers, a dielectric layer disposed between metal conducting layers, and at least one electrical connection extending between contact pads of metal conducting layers and through a through hole of the dielectric layer is provided. A system including at least one multi-layered electronic device, a satellite coupled to at least one multi-layered electronic device, and a controller hub electrically connected to the multi-layered electronic device via the satellite is also provided. A method of manufacturing the multi-layered electronic device including forming first and second first metal conducting layers, depositing a dielectric layer adjacent to the metal conducting layers, and connecting the metal conducting layers is also provided.

14 Claims, 11 Drawing Sheets

(51) Int. Cl.

| | | |
|---|---|---|
| *A61N 1/04* | (2006.01) | |
| *A61N 1/05* | (2006.01) | |
| *A61N 1/36* | (2006.01) | |
| *A61N 1/372* | (2006.01) | |
| *H05K 1/03* | (2006.01) | |
| *H05K 3/46* | (2006.01) | |
| *H05K 3/40* | (2006.01) | |
| *H05K 1/16* | (2006.01) | |
| *H05K 1/11* | (2006.01) | |
| *H01Q 1/38* | (2006.01) | |
| *H01Q 1/27* | (2006.01) | |

(52) U.S. Cl.
CPC ....... *A61N 1/3605* (2013.01); *A61N 1/36014* (2013.01); *A61N 1/37229* (2013.01); *H05K 1/0218* (2013.01); *H05K 1/0281* (2013.01); *H05K 1/0393* (2013.01); *H05K 1/11* (2013.01); *H05K 1/165* (2013.01); *H05K 3/0014* (2013.01); *H05K 3/4007* (2013.01); *H05K 3/4626* (2013.01); *H05K 3/4635* (2013.01); *H01Q 1/273* (2013.01); *H01Q 1/38* (2013.01); *H05K 2201/0133* (2013.01); *H05K 2201/0162* (2013.01); *H05K 2201/026* (2013.01); *H05K 2201/0323* (2013.01); *H05K 2201/09018* (2013.01); *H05K 2201/09563* (2013.01); *H05K 2201/09681* (2013.01); *H05K 2201/10098* (2013.01)

(58) Field of Classification Search
CPC ...... A61N 1/0472; A61N 1/0404; A61N 1/05; A61N 1/3605
USPC .......................................................... 607/60
See application file for complete search history.

(56) References Cited

U.S. PATENT DOCUMENTS

| | | | |
|---|---|---|---|
| 2009/0248129 A1* | 10/2009 | Keilman | A61N 1/37229 607/156 |
| 2012/0132458 A1 | 5/2012 | Sekine | |
| 2013/0150940 A1 | 6/2013 | Wilson et al. | |
| 2014/0135887 A1* | 5/2014 | Totman | A61B 5/04087 607/142 |
| 2014/0330355 A1 | 11/2014 | Stevenson et al. | |

OTHER PUBLICATIONS

International Search Report and Written Opinion in Application No. PCT/US2018/047362 dated Feb. 13, 2019.

\* cited by examiner

MULTI-LAYERED FABRICATION PROCESSING

CROSS-REFERENCE TO RELATED APPLICATION

This application claims priority under 35 U.S.C. § 119(e) to U.S. Provisional Application Ser. No. 62/548,310, titled "MULTI-LAYERED FABRICATION PROCESSING," filed on Aug. 21, 2017, which is incorporated herein by reference in its entirety for all purposes.

FIELD OF TECHNOLOGY

The disclosure relates to multi-layered electronic devices in general, and wearable or implantable multi-layered electronic devices in particular.

SUMMARY

Aspects and embodiments disclosed herein relate to multi-layered electronic devices. The multi-layered electronic devices may comprise two or more stacked metal conducting layers. Each metal conducting layer may comprise a trace and one or more contact pads. The multi-layered electronic devices may further comprise a dielectric layer. The dielectric layer may be disposed between metal conducting layers. The dielectric layer may comprise at least one through hole. The multi-layered electronic device may comprise at least one electrical connection extending between metal conducting layers. The at least one electrical connection may extend between the contact pads of metal conducting layers. The at least one electrical connection may extend through the at least one through hole of the dielectric layer. The multi-layered electronic device may comprise at least one insulating layer. The at least one insulating layer may be positioned adjacent to the at least one metal conducting layer. The at least one insulating layer may be positioned on an exterior surface of the multi-layered electronic device.

In some embodiments, each metal conducting layer may be coiled. In some embodiments, each metal conducting layer may have a uniform cross-sectional geometry.

The multi-layered electronic device may further comprise at least one support layer. The at least one support layer may be positioned adjacent to the insulating layer. The multi-layered electronic device may further comprise at least one ground layer. The at least one ground layer may be positioned adjacent to the at least one metal conducting layer. In some embodiments, the multi-layered electronic device may comprise at least two ground layers. The at least two ground layers may be positioned adjacent to the at least one metal conducting layer, for example, on opposite ends of the multi-layered electronic device.

In some embodiments, the multi-layered electronic device may comprise two oppositely disposed insulating layers. In other embodiments, the multi-layered electronic device may be arranged into a tubular structure and comprise a tubular insulating layer.

In some embodiments, the metal conducting layer may comprise a flexible metal foil or a thin film conductive ink. In some embodiments, the electrical connection may comprise a flexible metal foil or a thin film conductive ink. The metal conducting layer may comprise gold, platinum, or carbon nanotube ink. The electrical connection may comprise gold, platinum, or carbon nanotube ink.

In some embodiments, the dielectric layer may comprise silicon. In some embodiments, the insulating layer may comprise silicon.

In some embodiments, the metal conducting layer and dielectric layer may together have a thickness of about 100 µm or less.

The multi-layered electronic device may be configured to be an electrode, an antenna, or a connector.

In accordance with another aspect, there is provided an electronic system. The electronic system may be an in-vivo electronic system. For instance, the electronic system may be configured to be an implantable system. The electronic system may be configured to be a wearable system. In some embodiments, certain components of the electronic system are implantable. In some embodiments, certain components of the electronic system are wearable. The electronic system may comprise at least one multi-layered electronic device. The multi-layered electronic device may comprise two or more stacked metal conducting layers, each having a trace and one or more contact pads, a dielectric layer having at least one through hole and disposed between metal conducting layers, and at least one electrical connection extending between the contact pads of metal conducting layers and through the at least one through hole of the dielectric layer.

The electronic system may further comprise a satellite. The satellite may be coupled to at least one multi-layered electronic device. The electronic system may further comprise a controller hub. The controller hub may be electrically connectable to at least one multi-layered electronic device. The controller hub may be electrically connectable to the satellite. In some embodiments, the controller hub may be electrically connected to at least one multi-layered electronic device via the satellite.

In some embodiments, the controller hub is wirelessly connectable to at least one multi-layered electronic device. In some embodiments, the controller hub is wirelessly connectable to the satellite. In some embodiments, the satellite is wirelessly connectable to at least one multi-layered electronic device.

In some embodiments, the electronic system comprises a transmission line electrically connected to at least one multi-layered electronic device. The transmission line may be connected to the satellite. The transmission line may be connected to the controller hub.

In some embodiments, the at least one multi-layered electronic device of the electronic system may be configured to be an electrode, an antenna, or a connector. The at least one multi-layered electronic device may be configured to be directly secured to a subject. The at least one multi-layered electronic device may be arranged into a tubular structure and may comprise a tubular exterior insulating layer.

In accordance with yet another aspect, there is provided a method of manufacturing a multi-layered electronic device. The method may comprise forming a first metal conducting layer comprising a trace and one or more contact pads. The method may comprise depositing a dielectric layer adjacent to a metal conducting layer. The method may comprise forming a second metal conducting layer comprising a trace and one or more contact pads. The method may comprise positioning the second metal conducting layer adjacent to the dielectric layer, for example, on an opposite surface from the first metal conducting layer. The method may comprise creating through holes extending through the dielectric layer. The method may comprise connecting contact pads of metal conducting layers, for example, by providing an electrical connection extending through the dielectric layer through hole. The method may comprise laminating the multi-layered electronic device in an insulating material.

In some embodiments, connecting metal conducting layers comprises connecting by one of welding a flexible metal foil or depositing a conductive ink.

In some embodiments, the method further comprises folding the multi-layered electronic device into a tubular structure. In some embodiments, the method further comprises depositing a support layer adjacent to the first metal conducting layer. In some embodiments, the method further comprises depositing a ground layer adjacent to the first metal conducting layer.

BRIEF DESCRIPTION OF THE DRAWINGS

Various aspects of at least one embodiment are discussed below with reference to the accompanying figures, which are not intended to be drawn to scale. The figures are included to provide an illustration and a further understanding of the various aspects and embodiments, and are incorporated in and constitute a part of this specification, but are not intended as a definition of the limits of any particular embodiment. The drawings, together with the remainder of the specification, serve to explain principles and operations of the described and claimed aspects and embodiments. In the figures, each identical or nearly identical component that is illustrated in various figures is represented by a like numeral. For purposes of clarity, not every component may be labeled in every figure. In the figures:

DETAILED DESCRIPTION

Figure 1:
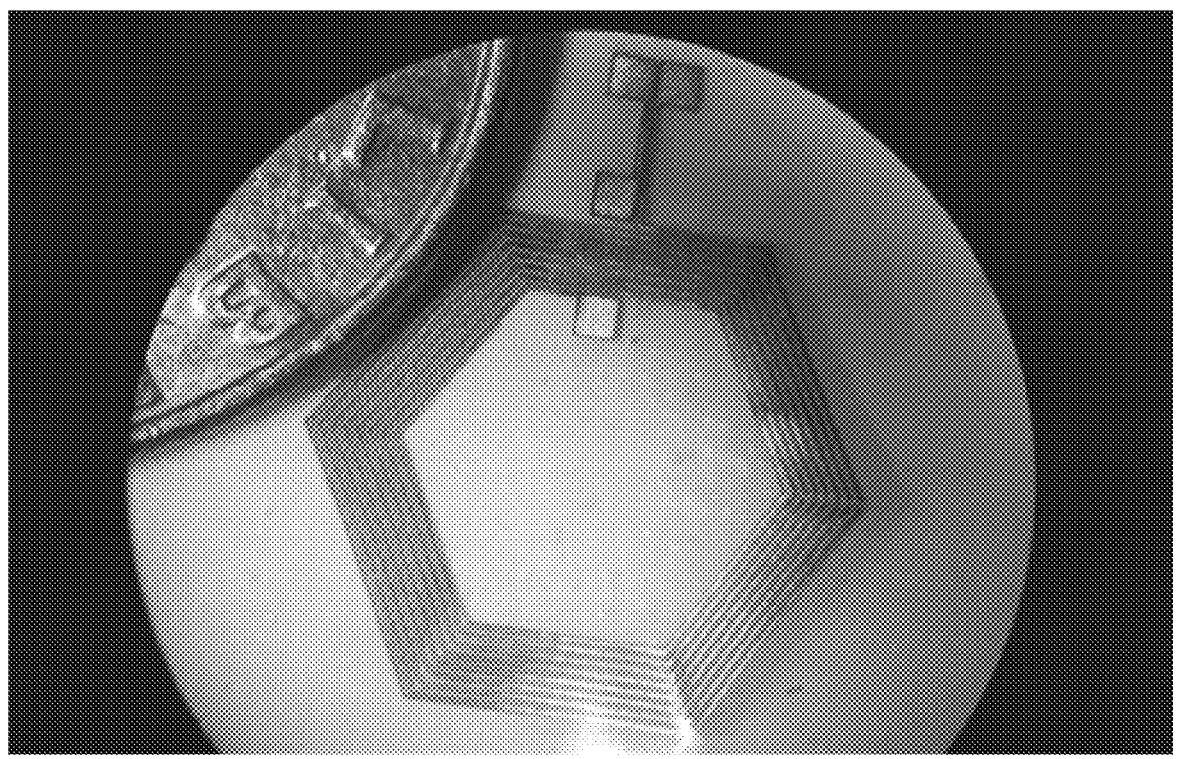
FIG. 1 is a photograph of a metal conducting layer of a multi-layered electronic device according to one embodiment, shown with a coin, for reference.

Complex electronic systems, specifically small-scale complex electronic systems, require the ability to efficiently connect multiple components. In particular, wearable or implantable devices require efficient connections to perform complex and robust electronic processes. Multi-layered electronic devices disclosed herein may provide the ability to build up multiple metal layers in a compact configuration for electrodes, interconnects, controlled transmission lines, shielded lines, and antennas. The electronic devices may simplify complex routing and crossing of electrical connections between components. The electronic devices may further be able to control electrical impedance and shielding of sensitive signal transmission, for example, in connection with a radio frequency signal (RF). With flexible solutions and layers, the electronic devices may further provide systems and components of systems that are able and/or designed to bend while performing. In particular, multi-layered electronic devices disclosed herein may provide a favorable and improved configuration for wearable or implantable electronic devices.

Wearable or implantable electronic devices may be used to stimulate a targeted tissue, for example, by delivering an electrical stimulation pulse to the targeted tissue in order to create a physiological response. In some embodiments, electronic systems or devices disclosed herein may be used to stimulate nerve or muscle tissue. For instance, electronic systems or devices disclosed herein may be used to stimulate peripheral nerves and/or cortical nerves. The stimulation may provide disease treatment, for example, to treat chronic pain, headaches (for example, migraines), Parkinson's disease, and psychological disorders (for example, depression).

Aspects and embodiments disclosed herein relate to multi-layered electronic devices. The multi-layered electronic devices may be wearable or implantable. The multi-layered electronic device may be configured to be directly secured to a subject, for instance as comprised in a wearable system or implanted into the subject. The multi-layered electronic devices may be a component of an electronic system. For example, the multi-layered electronic device may be configured to be an electrode, an antenna, or a connector. The multi-layered electronic device may be configured to be an interconnect (for example, to separate electronic devices), a transmission line (for example, a shielded transmission line), a connector (for example, a lead or module connection), an electrode for stimulation of monitoring of an electrical signal, a controlled impedance structure (for example, for an antenna), or a component to be used in combination with a multi-modal device or system (for example, multi-modal fluidics and optics).

In some embodiments, the multi-layered electronic devices comprise or consist of components constructed from bio-compatible materials. As used herein, bio-compatible materials refer to materials that will not initiate an immune or undesired physiological response within the body (for example, locally or systemically) when in contact with a target tissue. Such bio-compatible materials include, but are not limited to, metals, polymers, crystalline solids, and amorphous solids. Exemplary bio-compatible materials include platinum, gold, and silicon. Silicon-based exemplary bio-compatible materials include polymeric silicone and silicone elastomers. In some embodiments, stainless steel components may be included. For example, stainless steel wirings may be included.

The multi-layered electronic devices may be wearable or implantable. When worn or implanted the electronic devices may be subject to stresses and strains caused by the nearby or target tissues. Thus, the multi-layered electronic devices may generally be manufactured to withstand forces applied by muscle or nerve movement. In some embodiments, the multi-layered electronic devices may be manufactured to withstand a force of up to about 5 N. For example, the electronic devices may be manufactured to withstand an oscillatory force of up to about 2 N, up to about 3 N, up to about 4 N, or up to about 5 N. The electronic devices may be manufactured to withstand a pull force of up to about 2 N, up to about 2.5 N, up to about 3 N, up to about 3.5 N, or up to about 4 N.

The multi-layered electronic devices disclosed herein may comprise any number of repeating layers, as described. The devices may be scalable for their intended purpose. Specifically, the devices may be scalable on either end of the device by adding repeating layers to one or both ends of a multi-layered device. Each repeating layer may include two conductive layers with a shielding layer positioned between the conductive layers. The two conductive layers may communicate across the shielding layer via an electrical connection.

The multi-layered electronic devices may comprise two or more stacked metal conducting layers. Each metal conducting layer may comprise a trace and one or more contact pads. The trace and/or contact pad may be connected or connectable to one or more transmission line. The contact pads may have any cross-sectional area. In some embodiments, the contact pads have a substantially square cross-sectional area. The contact pads may have an area of about 1 $mm^2$. The contact pads may have an area of less than about 0.5 $mm^2$, less than about 1 $mm^2$, less than about 2 $mm^2$, or less than about 5 $mm^2$. In some embodiments, contact pads are positioned at one or more ends of a trace, for example, as shown in the photograph of FIG. 1.

The metal conducting layer may have a thickness of between about 5 μm and about 30 μm. For instance, the metal conducting layer may have a thickness of about 5 μm, about 10 μm, about 15 μm, about 20 μm, about 25 μm, or about 30 μm. In some embodiments, the metal conducting layer may have a thickness of less than about 25 μm, less than about 20 μm, less than about 15 μm, less than about 10 μm, or less than about 5 μm.

Each metal conducting layer may be substantially planar. In some embodiments, each metal conducting layer may be partially or entirely coiled, for example, as shown in the photograph of FIG. 1. For a partially or entirely coiled metal conducting layer, the trace width and spacing may be about 50 μm. In some embodiments, the metal conducting layer trace width and spacing is more than about 50 μm. In some embodiments, each metal conducting layer may have a uniform cross-sectional geometry. The cross-sectional geometry of the metal conducting layer may be configured to ensure uniform characteristic impedance along its length. The uniform cross-sectional geometry may include a substantially circular, substantially rectangular, substantially pentagonal, substantially hexagonal, substantially heptagonal, substantially octagonal, or other uniform cross-sectional geometry. In some embodiments, the cross-sectional geometry is defined by a coiled trace of slightly increasingly greater radius.

In some embodiments, the metal conducting layer may comprise or be formed from a flexible metal foil or a thin film conductive ink. The metal conducting layer may comprise or consist of a noble metal conductor or a plurality of noble metal conductors. In some embodiments, the metal conducting layer may comprise or consist of gold, platinum, or carbon nanotube ink. The metal conducting layer may be substantially flexible, such that the multi-layered electronic device is substantially flexible when all layers are incorporated. A transmission line may comprise or be formed from the same material or a different material as the metal conducting layer. For instance, a transmission line may comprise or be formed from a flexible metal foil or a thin film conductive ink, for example, gold, platinum, or carbon nanotube ink. The transmission line may be substantially rigid or substantially flexible.

The multi-layered electronic devices may further comprise a dielectric layer. The dielectric layer may be disposed between metal conducting layers. In some embodiments, the dielectric layer may be deposited as a coating on the metal conducting layer. For instance, the metal conducting layer may be coated or embedded in the dielectric layer substrate. As disclosed herein, the dielectric layer may function as an insulating layer between metal conducting layers. The dielectric layer may be slightly polarized by an electric field, but electric charges may not flow through the dielectric layer. The dielectric layer may comprise or consist of a dielectric material. The dielectric layer may comprise or consist of a flexible polymer. The dielectric layer may comprise a polymeric layer of insulation. In some embodiments, the dielectric layer may comprise silicon.

The dielectric layer may have a thickness of between about 50 μm and about 500 μm. For instance, the dielectric layer may have a thickness of about 50 μm, about 100 μm, about 150 μm, about 200 μm, about 250 μm, about 300 μm, about 350 μm, about 400 μm, about 450 μm, or about 500 μm. In some embodiments, the dielectric layer may have a thickness of less than about 500 μm, less than about 450 μm, less than about 400 μm, less than about 350 μm, less than about 300 μm, less than about 250 μm, less than about 200 μm, less than about 150 μm, less than about 100 μm, or less than about 50 μm.

In some embodiments, the metal conducting layer and dielectric layer may together have a thickness of about 100 μm or less. For instance, the metal conducting layer and dielectric layer may together have a thickness of about 50 μm, about 55 μm, about 60 μm, about 65 μm, about 70 μm, about 75 μm, about 80 μm, about 85 μm, about 90 μm, about 95 μm, or about 100 μm.

The dielectric layer may comprise at least one through hole. As disclosed herein, a through hole may be any opening extending across or through a material. The dielectric layer through holes may provide an opening to extend a connection between metal conducting layers positioned on opposite sides of the dielectric layer. Through holes may be added to build up the multi-layered electronic device on either end. Through holes may comprise any size or shape as necessary to extend the connection between metal conducting layers.

The multi-layered electronic device may comprise at least one electrical connection. The at least one electrical connection may extend between the contact pads of metal conducting layers, or between contact pads of the same metal conducting layer (for example, to function as a connector bridge). The multi-layered electronic device may comprise at least one electrical connection extending between metal conducting layers, for example via the at least one through hole of the dielectric layer. The electrical connections may efficiently and robustly provide connection between the various stacked metal conducting layers. The electrical connection may comprise or be formed from a flexible metal foil or a thin film conductive ink, as previously described with respect to the metal conducting layer. For instance, the electrical connection may comprise gold, platinum, or carbon nanotube ink. The electrical connection may comprise a conductive epoxy. In some embodiments, the electrical connection may have a thickness that is substantially similar or lower than the thickness of the metal conducting layer.

The multi-layered electronic device may comprise at least one insulating layer. The at least one insulating layer may be positioned adjacent to the at least one metal conducting layer. The at least one insulating layer may be positioned on an exterior surface of the multi-layered electronic device. In some embodiments, the at least one insulating layer may partially, completely, or substantially completely encapsulate the multi-layer electronic device. For instance, the multi-layered electronic device may comprise two oppositely disposed insulating layers.

In some embodiments, the multi-layered electronic device may be arranged into a tubular structure and comprise a tubular insulating layer. The tubular structure may be achieved by folding, coiling, or rolling the multi-layered electronic device. A flat multi-layered electronic device may have a thickness of about 100 µm. In some embodiments, a tubular multi-layered electronic device may have a radius of between about 100 µm and about 500 µm, for example, between about 200 µm and about 250 µm.

The multi-layered electronic device may be configured to have a three-dimensional geometry that is advantageous for its intended purpose. For instance, an electrode may comprise a substantially planar three-dimensional geometry with a large cross-sectional surface area. A coiled three-dimensional geometry may be advantageous for flexible cabling, antenna transmission, mating (for example, to separate components), or connectors. The multi-layer electronic device may have a three-dimensional geometry that is advantageous for bending around structures (for example, target tissues or bodily tissues) or for attaching or conforming to an external structure.

The insulating layer may comprise the same or a different material as the dielectric layer. In some embodiments, the insulating layer may serve to partially, completely, or substantially completely insulate the interior components of the multi-layer electronic device. The insulating layer may comprise one or more through hole, as described with respect to the dielectric layer. The one or more through hole may provide a connection with an exterior component (for example, an exterior transmission line) or a device configured to be coupled to the multi-layered electronic device. The insulating layer may comprise or consist of a dielectric material. The insulating material may comprise or consist of a fully insulating material. The insulating layer may comprise or consist of a flexible polymer. The insulating layer may comprise a polymeric layer of insulation. In some embodiments, the insulating layer may comprise silicon.

The insulating layer may have a thickness as previously described with respect to the dielectric layer. For example, the insulating layer may have a thickness of between about 50 µm and about 500 µm. The insulating layer may have a thickness of about 50 µm, about 100 µm, about 150 µm, about 200 µm, about 250 µm, about 300 µm, about 350 µm, about 400 µm, about 450 µm, or about 500 µm. In some embodiments, the insulating layer may have a thickness of less than about 500 µm, less than about 450 µm, less than about 400 µm, less than about 350 µm, less than about 300 µm, less than about 250 µm, less than about 200 µm, less than about 150 µm, less than about 100 µm, or less than about 50 µm.

The multi-layered electronic device may further comprise at least one support layer. The at least one support layer may be positioned adjacent to the insulating layer. The at least one support layer may provide structural support to the multi-layered electronic device. However, in some embodiments, the multi-layered electronic device comprising a support layer is substantially flexible. The at least one support layer may be in the form of a mesh material. The at least one support layer may comprise a polymer (for example, silicon) or a metal (for example, to form a shield for electromagnetic fields). In some embodiments, the support layer has a thickness of at least about 25 µm. The support layer may have a thickness of about 10 µm, about 15 µm, about 20 µm, about 25 µm, about 30 µm, about 35 µm, about 40 µm, about 45 µm, or about 50 µm.

The multi-layered electronic device may further comprise at least one ground layer. The at least one ground layer may be positioned adjacent to the at least one metal conducting layer. In some embodiments, the multi-layered electronic device may comprise at least two ground layers. The at least two ground layers may be positioned adjacent to the at least one metal conducting layer, for example, on opposite ends of the multi-layered electronic device. The at least one ground layer may be provided for the purpose of creating a shield for electromagnetic fields. For instance, the at least one ground plane may shield electromagnetic fields originating from the interior layers of the multi-layered electronic device. The at least one ground layer may reduce energy loss to the surrounding environment.

Figure 3:
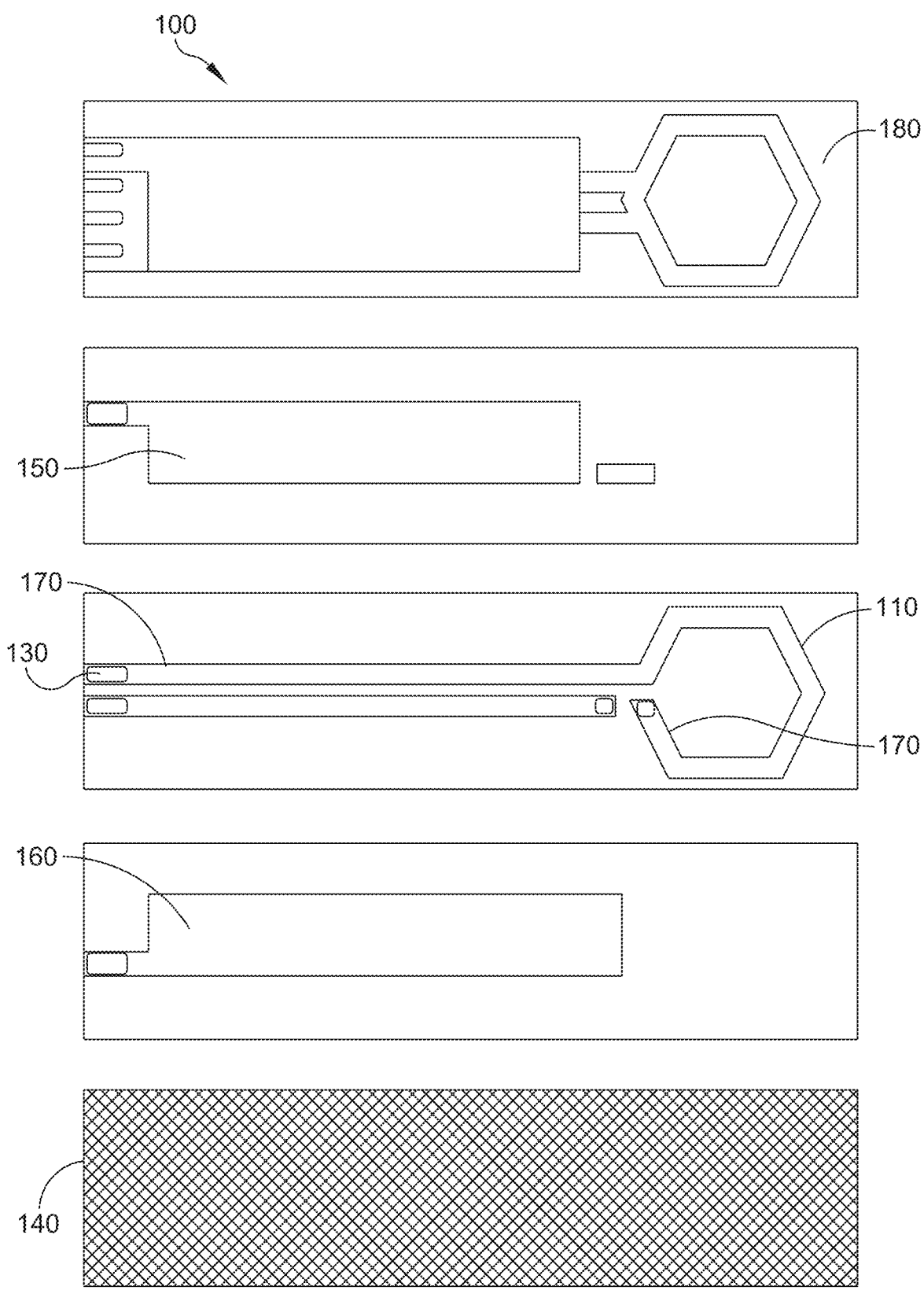
FIG. 3 is a top exploded view schematic drawing of multiple layers of a multi-layered electronic device, according to one embodiment.

The at least one ground layer may be constructed of the same or different material, and have the same or different thickness, as the metal conducting layer. In some embodiments, the at least one ground layer comprises a connection pad (for example, as shown in FIG. 3). The at least one ground layer may comprise a material or thickness as previously described with respect to the metal conducting layer. For example, the at least one ground layer may comprise or be formed from a flexible metal foil or a thin film conductive ink. The ground layer may comprise or consist of a noble metal conductor or a plurality of noble metal conductors. In some embodiments, the ground layer may comprise or consist of gold, platinum, or carbon nanotube ink. The at least one ground layer may have a thickness of between about 5 µm and about 30 µm. For instance, the ground layer may have a thickness of about 5 µm, about 10 µm, about 15 µm, about 20 µm, about 25 µm, or about 30 µm. In some embodiments, the ground layer may have a thickness of less than about 25 µm, less than about 20 µm, less than about 15 µm, less than about 10 µm, or less than about 5 µm.

The multi-layered electronic devices disclosed herein may be partially implantable, partially wearable, or both. In accordance with certain embodiments, the multi-layered electronic devices disclosed herein may contain an intrafascicular portion and a cuff portion. The intrafascicular portion may be configured to be positioned within a target tissue, for example, within a fascicle. The cuff portion may be configured to be positioned on a surface of the target tissue or otherwise exterior to the target tissue. In some embodiments, the intrafascicular portion and the cuff portion may comprise substantially the same materials.

The multi-layered electronic devices may be configured to exhibit a desired impedance that is advantageous for its intended purpose. The electronic device may be configured to exhibit an impedance between about 50 kΩ and 200 kΩ. In some embodiments, the electronic device may comprise an intrafascicular portion and a cuff portion. The intrafascicular portion and the cuff portion may be configured to exhibit the same or different impedances. In some embodiments, the intrafascicular portion may be configured to exhibit an impedance between about 50 kΩ and 200 kΩ. The cuff portion may be configured to exhibit a lower impedance. For example, the cuff portion may be configured to exhibit an impedance between about 1 kΩ and 4 kΩ.

In accordance with another aspect, there is provided an electronic system. The electronic system may be an in-vivo electronic system. For instance, the electronic system may be configured to be an implantable system. In some embodiments, the electronic system comprises or consists of components constructed from bio-compatible materials. The electronic system may be configured to be a wearable system. Certain components of the electronic system may be implantable or wearable, for example, such that certain components of the system are implanted and communicating with components of the system which are wearable or externally coupled to a subject.

The electronic system may comprise at least one multi-layered electronic device, as previously described herein. For instance, the multi-layered electronic device may comprise two or more stacked metal conducting layers, each having a trace and one or more contact pads, a dielectric layer having at least one through hole and disposed between metal conducting layers, and at least one electrical connection extending between the contact pads of metal conducting layers and through the at least one through hole of the dielectric layer. The system may comprise a plurality of multi-layered electronic devices coupled to each other or coupled to another component of the system.

The electronic system may further comprise a satellite. The satellite may be coupled to at least one multi-layered electronic device. The satellites may enable communication between a plurality of multi-layered electrical devices, for example for real-time recording or stimulation.

The electronic system may further comprise a controller hub. The controller hub may provide power to the other components of the system. The satellite and/or controller hub may enable transmission of signals to and from the multi-layered electronic devices, may provide channels for the multi-layered electronic devices to communicate with other components of the system, and/or may include one or more processors for closed-loop control (for example, adaptive control) or bidirectional telemetry.

The controller hub may be electrically connectable to at least one multi-layered electronic device. The controller hub may be electrically connectable to the satellite. In some embodiments, the controller hub may be electrically connected to at least one multi-layered electronic device via the satellite. In some embodiments, the controller hub is wirelessly connectable to at least one multi-layered electronic device. In some embodiments, the controller hub is wirelessly connectable to the satellite. In some embodiments, the satellite is wirelessly connectable to at least one multi-layered electronic device. In other embodiments, the electronic system may comprise a transmission line electrically connected to at least one multi-layered electronic device. The transmission line may be connected to the satellite. The transmission line may be connected to the controller hub.

The electronic system may comprise any combination of wireless and line electrical connections between the various components.

The electronic system may further comprise a base hub. The base hub may be electrically connectable to the controller hub, as previously described. In some embodiments, particularly in embodiments wherein the controller hub is implanted or implantable, the base hub may be an externally located controller configured to relay information to the implanted controller hub. The base hub may be capable of providing any of the control functions previously described with respect to the satellite and controller hub.

In accordance with yet another aspect, there is provided a method of manufacturing a multi-layered electronic device. The method may comprise forming and/or depositing multiple layers of a multi-layered electronic device. The method may be scalable for manufacturing and allow more complex designs of electronic devices by layering the multi-layer structures.

The method may comprise forming a metal conducting layer comprising a trace and one or more contact pads. The metal conducting layer may be formed from a thin film metal conductor, as previously described. In some embodiments, forming the metal conducting layer comprises etching the metal conductor from a thin film sheet of a conducting metal, for example as shown in FIGS. 4-8. In some embodiments, forming a metal conducting layer comprises depositing a conductive ink or epoxy on a substrate (for example, on the dielectric layer substrate) in a desired configuration.

The method may comprise forming a dielectric layer, as previously described. The dielectric layer may be deposited adjacent to a metal conducting layer. In some embodiments, the metal conducting layer is formed adjacent to the dielectric layer. The method may comprise creating through holes extending through the dielectric layer. The through holes may be created in any size and shape to facilitate connection between metal conducting layers on opposite sides of the dielectric layer.

The method may comprise forming and/or positioning a second metal conducting layer adjacent to the dielectric layer, for example, on an opposite surface from the first metal conducting layer. In some embodiments, the method may comprise forming subsequent metal conducting and dielectric layers in this fashion until the multi-layered electronic device comprises a desired number of stacked metal conducting layers.

The method may comprise connecting contact pads of metal conducting layers, for example, by providing an electrical connection extending through the dielectric layer through hole. In some embodiments, connecting metal conducting layers comprises connecting by one of welding (for example, resistance welding, spot welding, or laser welding) a flexible metal foil or depositing a conductive ink or epoxy. Connecting metal conducting layers may comprise brazing metal materials. Connecting metal conducting layers may comprise pneumatically dispensing a conductive ink or epoxy. Connecting metal conducting layers may comprise printing a conductive ink or epoxy, for example via an aerosol jet printer. Connecting metal conducting layers may comprise sputtering an electrical connection layer through an annular ring (for example, a shadow mask). Connecting metal conducting layers may comprise depositing an epoxy material with a metal foil. Connecting metal conducting layers may comprise wire bonding the contact pads of metal conducting layers. The method may comprise connecting contact pads of metal conducting layers until all stacked metal conducting layers of the multi-layered electronic device are connected. In some embodiments, the method may comprise connecting metal conducting layers of the multi-layered electronic device with other components, for example transmission lines (exterior or interior transmission lines).

The method may comprise laminating the multi-layered electronic device in an insulating material, for example by coating the device. The insulating material may be any insulating material, as previously descried.

In some embodiments, the method further comprises depositing a support layer adjacent to the first metal conducting layer. The support layer may be any support layer, as previously described.

In some embodiments, the method further comprises depositing a ground layer adjacent to the first metal conducting layer. The ground layer may be deposited by any method as previously described with respect to the metal conducting layers. In some embodiments, the ground layer may be electrically connected to a metal conducting layer or transmission line by any of the methods as previously described.

In some embodiments, the method further comprises forming and/or depositing a transmission line adjacent to the first metal conducting layer. The transmission line may be formed and/or deposited by any method as previously described with respect to the metal conducting layers. In some embodiments, the transmission line may be electrically connected to a metal conducting layer or ground layer by any of the methods as previously described.

In some embodiments, the method further comprises folding the multi-layered electronic device into a three-dimensional structure. The three-dimensional structure may be designed, selected, or configured to be advantageous for the intended purpose of the multi-layered electronic device, as previously described. In some embodiments, the method comprises folding the multi-layered electronic device into a tubular structure, for example, by coiling, rolling, or folding. The method may comprise laminating the multi-layered electronic device in an insulating material before or after folding the device into a three-dimensional structure.

With particular reference to the figures, FIG. 1 is a photograph of a metal conducting layer of a multi-layered electronic device according to one exemplary embodiment. The metal conducting layer shown in FIG. 1 is coiled. Several contact pads and a trace can be seen in the exemplary metal conducting layer of FIG. 1. In the photograph, the exemplary metal conducting layer is shown with a coin, for size reference.

Figure 2:
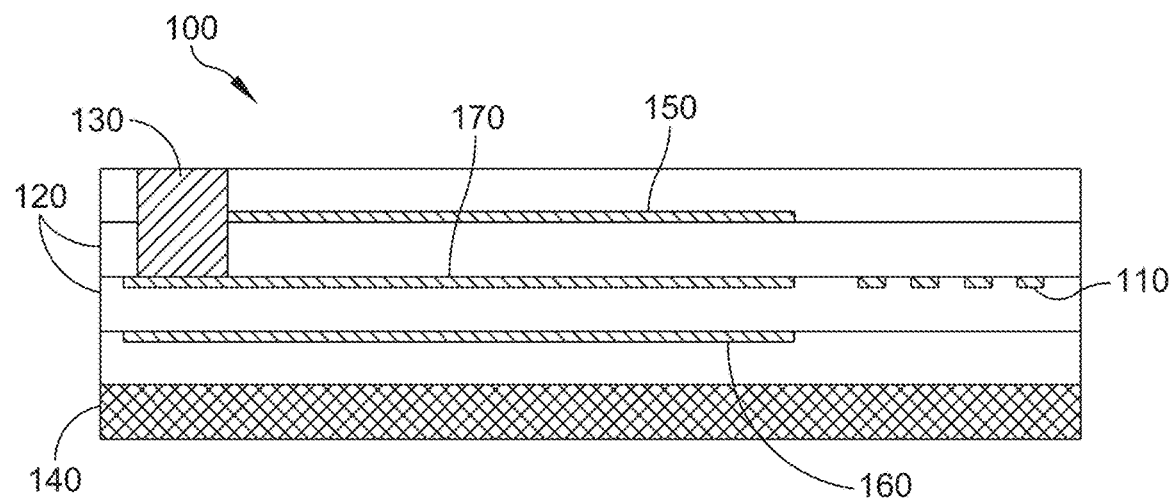
FIG. 2 is a side view schematic drawing of a multi-layered electronic device, according to one embodiment.

FIGS. 2 and 3 are schematic diagrams of a multi-layered electronic device 100, showing multiple layers and an exemplary arrangement of layers. FIG. 2 is a side view of the exemplary multi-layered electronic device 100. FIG. 3 is a top exploded view of several layers of the exemplary multi-layered electronic device 100. The exemplary multi-layered electronic devices 100 of FIGS. 2 and 3 include a metal conductor layer 110, a plurality of dielectric layers 120, a plurality of contact pads 130 (seen, for example, on the transmission line 170, metal conductor layer 110, and ground layers 150, 160 of FIG. 3), a plurality of traces (seen, for example, on the transmission line 170 and metal conductor layer 110 of FIG. 3), a support layer 140, a top ground 150, a bottom ground 160, a transmission line 170, and an insulating layer 180.

Figure 4:
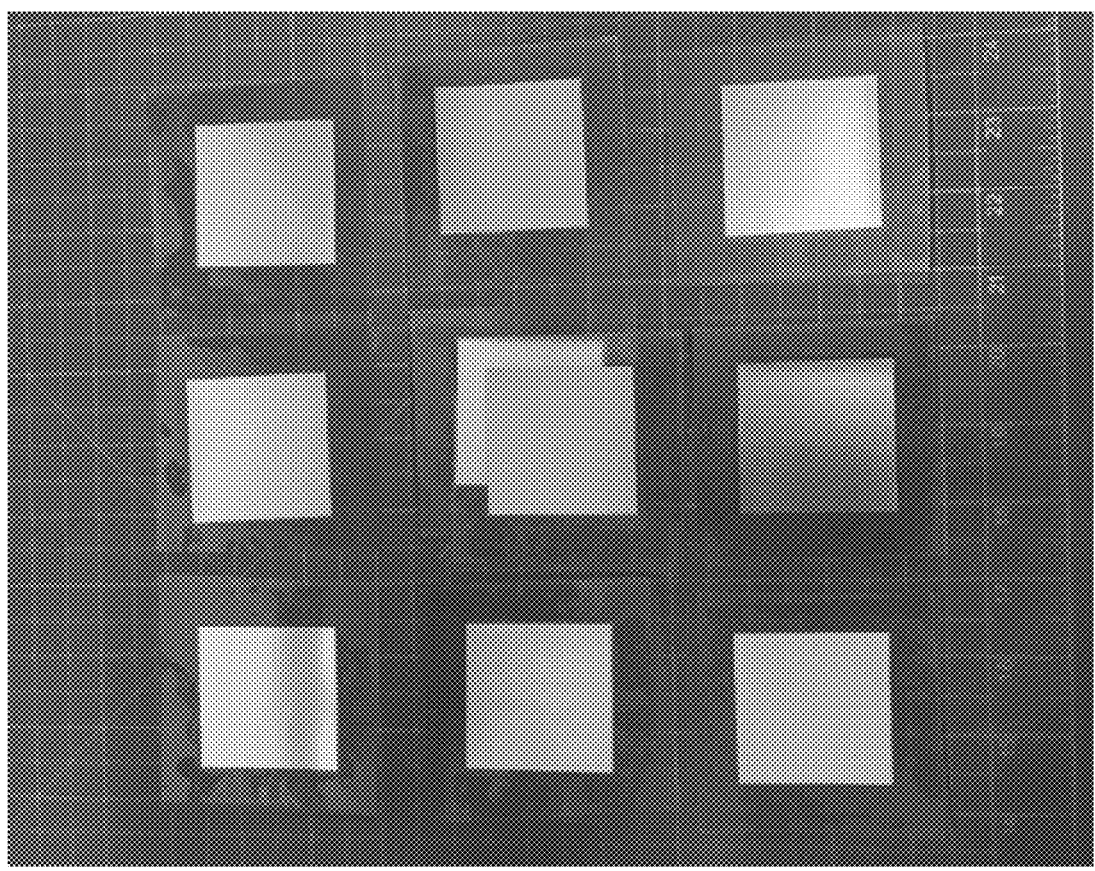
FIG. 4 is a photograph of a component of a multi-layered electronic device, during one step of a method for manufacturing a multi-layered electronic device, according to one embodiment.
Figure 5:
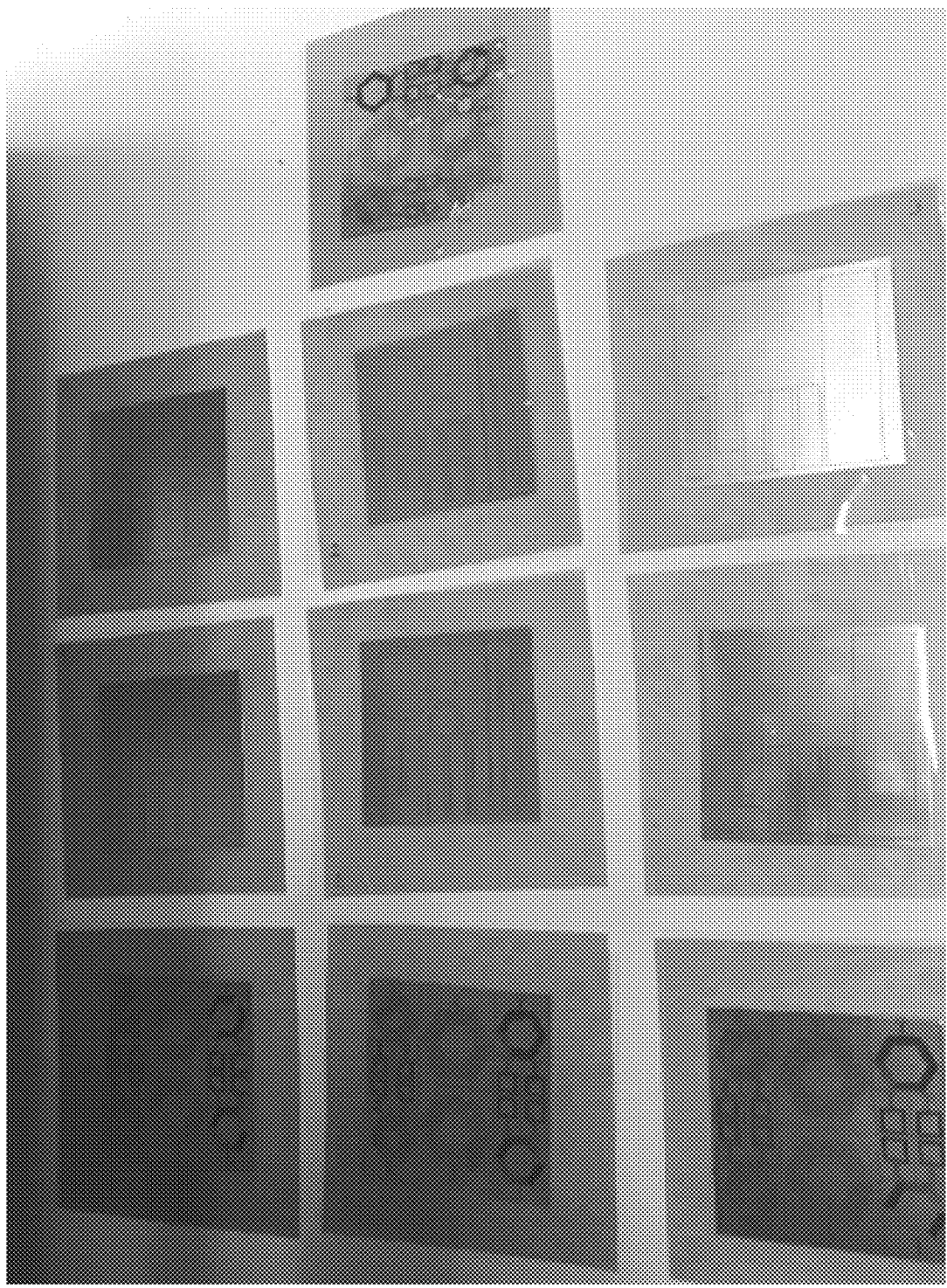
FIG. 5 is a photograph of a component of a multi-layered electronic device, during another step of a method for manufacturing a multi-layered electronic device, according to one embodiment.
Figure 6:
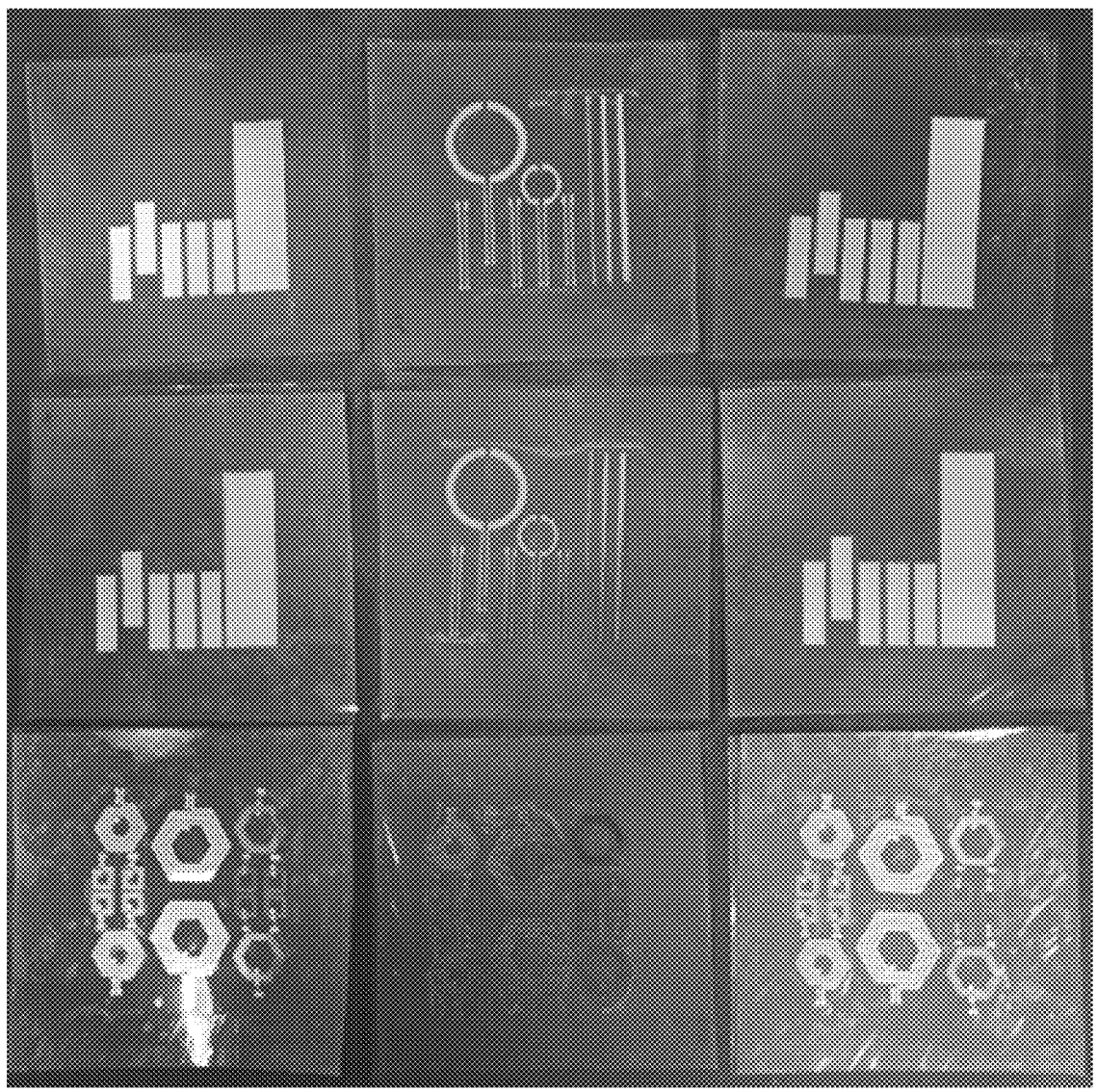
FIG. 6 is a photograph of a component of a multi-layered electronic device, during another step of a method for manufacturing a multi-layered electronic device, according to one embodiment.
Figure 7:
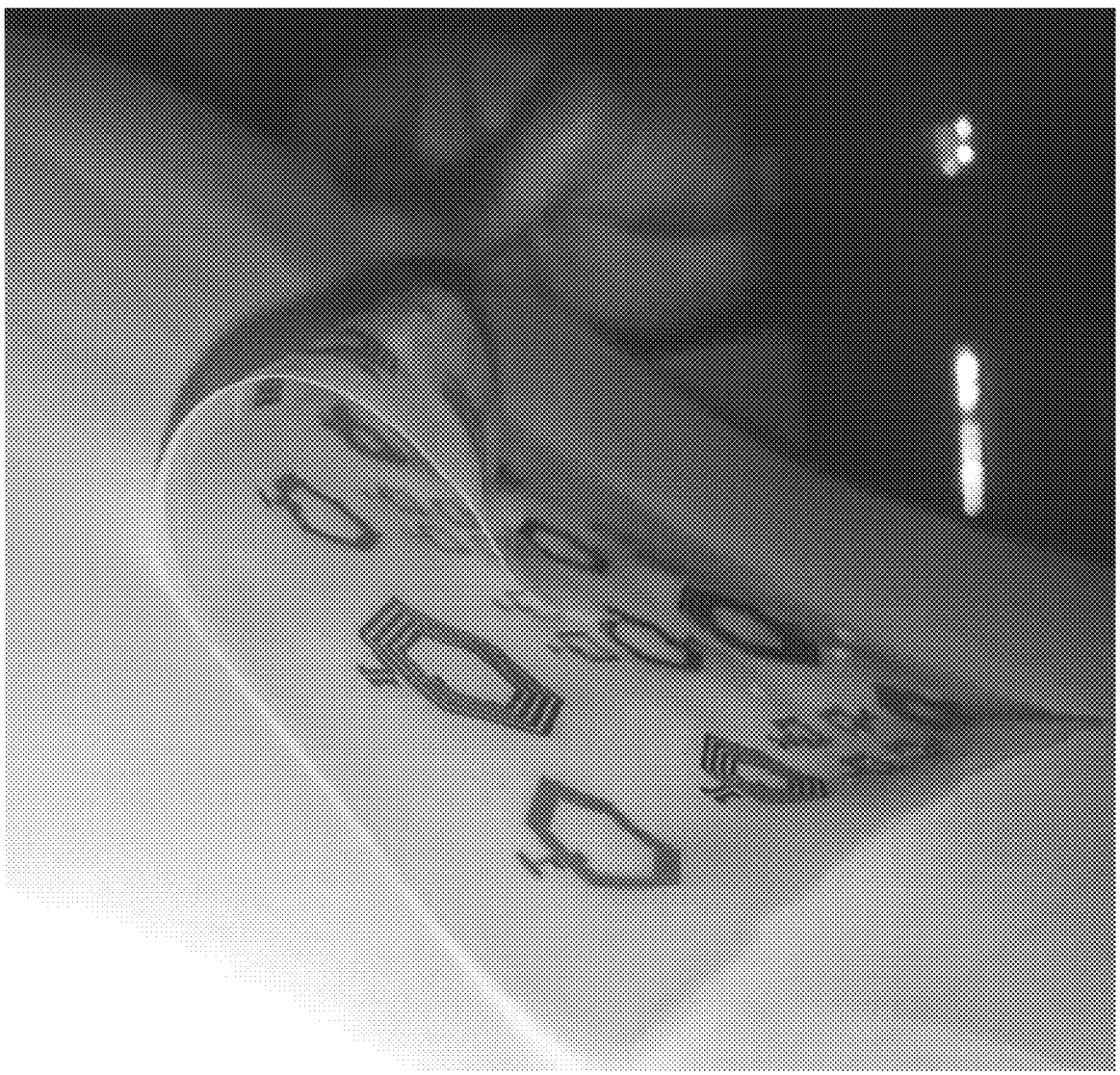
FIG. 7 is a photograph of a component of a multi-layered electronic device, during another step of a method for manufacturing a multi-layered electronic device, according to one embodiment.
Figure 8:
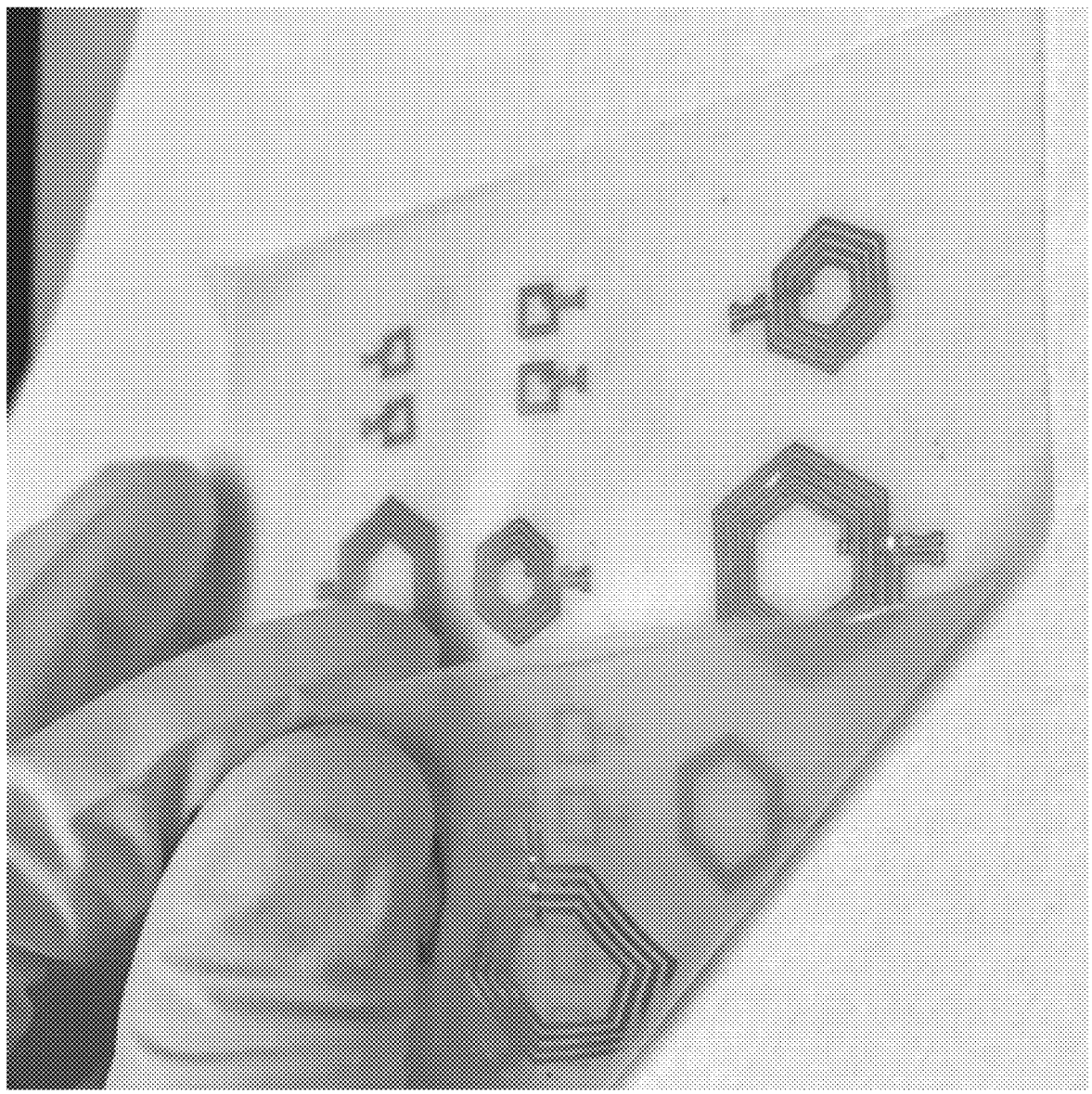
FIG. 8 is a photograph of a component of a multi-layered electronic device, during another step of a method for manufacturing a multi-layered electronic device, according to one embodiment.

FIGS. 4-8 are photographs of several components of a multi-layered electronic device during an exemplary manufacturing method. Specifically, as shown in the photograph of FIG. 4, thin film gold is formed on release tape. As shown in the photograph of FIG. 5, components of an exemplary multi-layered device are etched on the thin film gold of FIG. 4. The exemplary components can be seen in the photograph of FIG. 6. The photographs of FIGS. 7 and 8 provide context for the exemplary gold components of the multi-layered electronic device on release tape.

Figure 9:
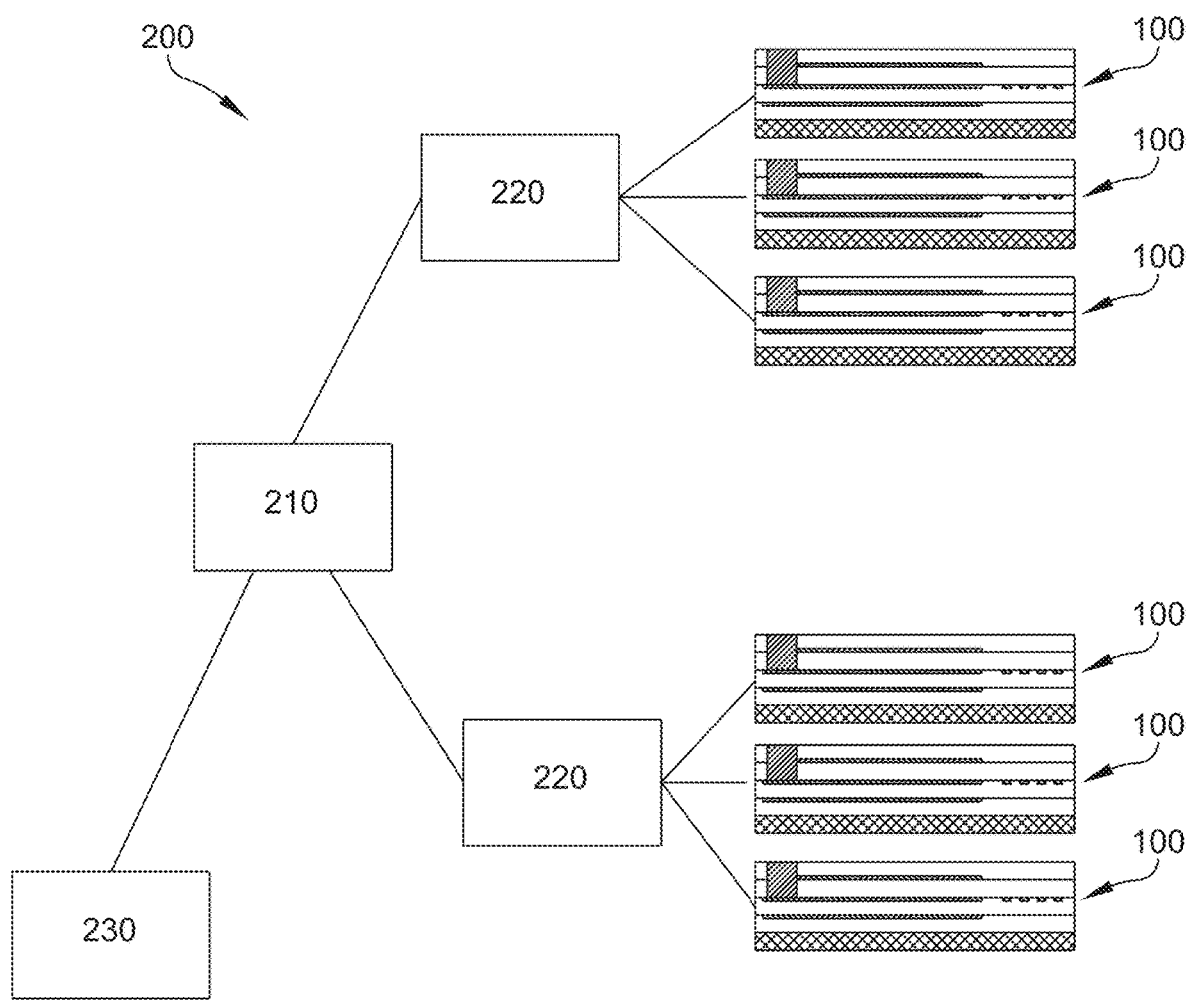
FIG. 9 is a schematic drawing of an electronic system, according to one embodiment.

FIG. 9 is a schematic drawing of an exemplary electronic system 200. The exemplary electronic system 200 of FIG. 9 includes a plurality of multi-layered electronic devices 100, a plurality of satellites 220 electrically connected to the multi-layered electronic devices, a controller hub 210 electrically connected to the satellites, and a base hub 230 electrically connected to the controller hub. The electrical connections shown in the system of FIG. 9 may be physical or wireless connections.

EXAMPLES

Example 1: Mechanical Data, Oscillatory Test

Multi-layered electronic devices fabricated according to the methods disclosed herein were subjected to oscillatory tests to determine mechanical strength. The oscillations were performed at frequencies of 10 Hz or 3 Hz by applying a force of 1N or 0.5 N at an amplitude of 20 µm, 50 µm, or 100 µm. The number of cycles withstood by each electronic device until failure were recorded. In some instances, failure did not break the electronic device. The results of the oscillatory tests are presented in Table 1.

TABLE 1

Oscillatory Test Data

| Sample | Frequency (Hz) | Force (N) | Amplitude (µm) | Cycles Until Fail |
|---|---|---|---|---|
| 1-1 | 10 | 1 | 20 | 34,800 |
| 1-2 | 10 | 1 | 100 | 3,300 |
| 1-3 | 10 | 1 | 100 | 1,800 |
| 1-4 | 10 | 1 | 100 | 12,000 |
| 1-5 | 10 | 0.5 | 50 | 96,000* |
| 1-6 | 10 | 1 | 50 | 5,400 |
| 1-7 | 10 | 1 | 50 | 54,000 |
| 1-8 | 10 | 1 | 50 | 4,500 |
| 2-1 | 3 | 1 | 50 | 27,000* |
| 2-2 | 3 | 1 | 50 | 23,400* |
| 2-3 | 3 | 1 | 50 | 3,960 |
| 2-4 | 3 | 1 | 50 | 14,760 |
| 2-5 | 3 | 1 | 50 | 9,900 |
| 2-6 | 3 | 1 | 50 | 23,400* |
| 3-1 | 3 | 1 | 50 | 23,400* |
| 3-2 | 3 | 1 | 50 | 23,400* |
| 3-3 | 3 | 1 | 50 | 23,400* |
| 4-1 | 3 | 1 | 50 | 1,260 |
| 4-2 | 3 | 1 | 50 | 23,400* |
| 4-3 | 3 | 1 | 50 | 23,400* |

*Sample did not break at failure

The exemplary electronic devices (samples 1 through 4) were prepared from platinum foil, epoxy resin, silicone, and contained stainless steel wirings. The mesh pattern and lamination thicknesses were varied by sample.

Certain target tissues may move up to 1 cm at max flexion. Assuming a stress of about 800,000 N/m$^2$ and an area of about $4.0 \times 10^{-6}$ m$^2$, it is estimated that these exemplary electronic devices can withstand a maximum force of up to about 3 N.

Accordingly, the bio-compatible multi-layered electronic devices disclosed herein are capable of withstanding oscillatory forces caused by nearby and target tissues when worn or implanted.

Example 2: Mechanical Data, Static Pull Test

Multi-layered electronic devices fabricated according to the methods disclosed herein were subjected to static pull tests to determine mechanical strength. The devices were pulled at varying forces. The force required to break each device was measured. The results of the static pull tests are presented in Table 2.

TABLE 2

Static Pull Test Data

| Sample | Force to Break Sample (N) |
|---|---|
| 1-1 | 1.95 |
| 1-2 | 2.02 |
| 1-3 | 2.10 |
| 1-4 | 2.39 |
| 1-5 | 1.06 |
| 1-6 | 2.25 |
| 2-1 | 1.84 |
| 2-2 | 2.37 |
| 2-3 | 2.20 |
| 2-4 | 2.04 |
| 2-5 | 1.80 |
| 3-1 | 3.57 |
| 3-2 | 3.18 |
| 3-3 | 4.37 |
| 3-4 | 3.04 |
| 3-5 | 3.10 |
| 4-1 | 3.40 |
| 4-2 | 2.97 |
| 4-3 | 2.79 |
| 4-4 | 2.07 |
| 4-5 | 2.14 |

The electronic devices labeled samples 1 through 4 were prepared as described in example 1.

On average, samples 1 and 2 broke at a pull strength of 2.00 N, while samples 3 and 4 broke at a pull strength of 3.06 N. Thus, in accordance with certain embodiments, the electronic devices disclosed herein can withstand a pull strength of at least 2 N, for example, at least 2.07 N. In some embodiments, the electronic devices can withstand a pull strength of about 2.5 N, about 3 N, about 3.5 N, or about 4 N.

Accordingly, the electronic devices prepared by the methods disclosed herein are capable of withstanding pull forces caused by nearby and target tissues when worn or implanted.

Figure 10:
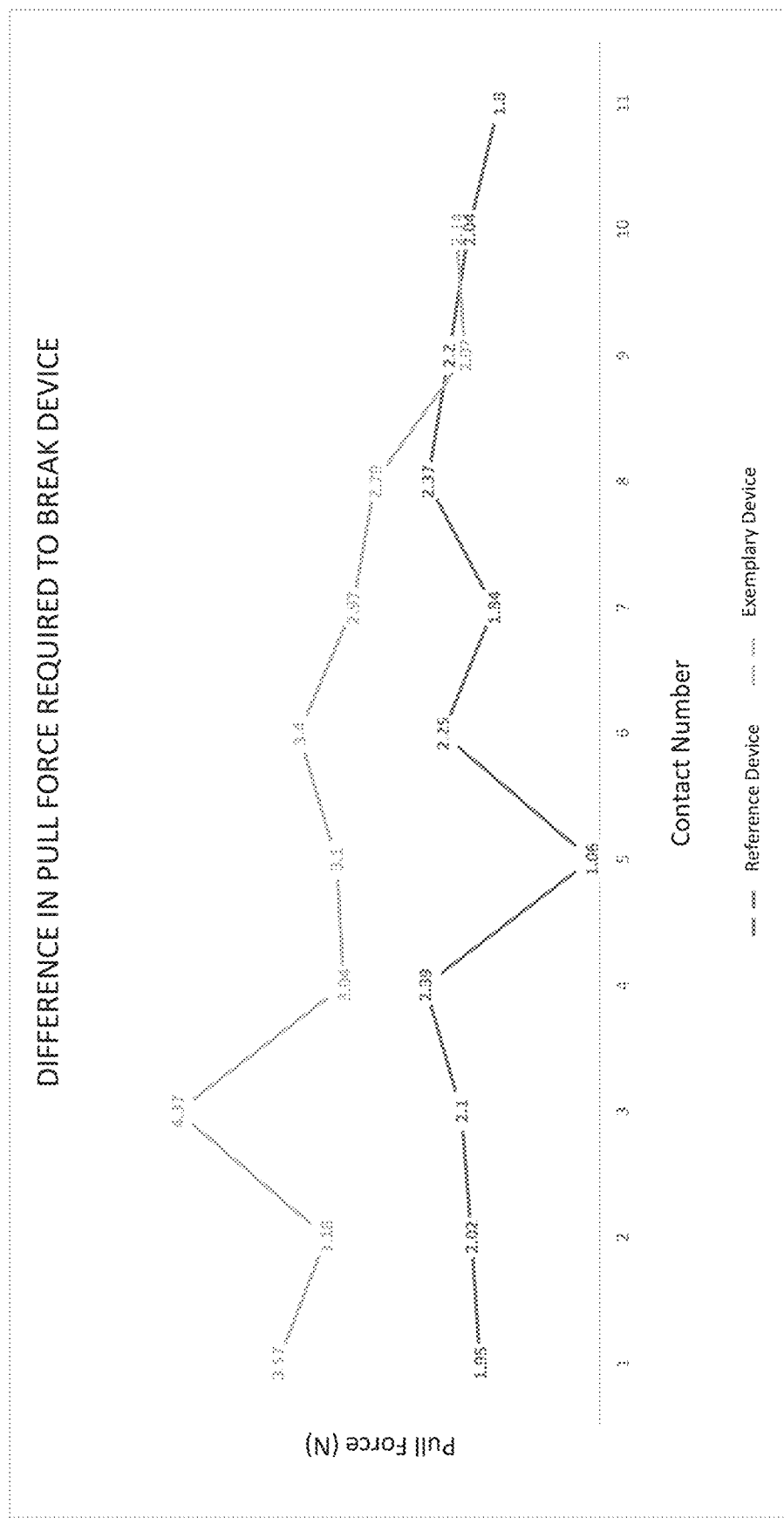
FIG. 10 is a graph of mechanical strength of exemplary electronic devices shown as the pull force required to break the exemplary electronic device.

Additionally, as shown in the graph presented in FIG. 10, the electronic devices prepared by modifying the mesh pattern (samples 3 and 4) can withstand a greater pull strength than the first two sets of samples. It was determined that the electronic devices with the modified mesh pattern show a 1.5 to 2× improvement in mechanical strength when subjected to pull forces. In some embodiments, the mesh pattern may be selected to correlate with an expected pull strength of the desired target tissue.

Example 3: Performance Data, Impedance Test

Multi-layered electronic devices fabricated according to the methods disclosed herein were subjected to impedance tests to determine performance. The electrical devices were subjected to a frequency of 1 kHz. The electrical devices were subjected to a 24-hour soak in a standard saline solution including salts and ions and a composition and concentration to mimic human bodily fluids. The impedance was measured by electrochemical impedance spectroscopy (EIS). The results for a first and second batch of testing are presented in Tables 3 and 4, respectively.

TABLE 3

EIS Test Data, Batch 1

| Sample | Impedance at 1 kHz before soak ($\Omega$) | Impedance at 1 kHz after soak ($\Omega$) |
|---|---|---|
| I1 | 28,724.06112 | 19,436.779 |
| I2 | 137,079.8343 | 114,469.3745 |
| I3 | 113,390.3054 | 105,706.3066 |
| I4 | 110,908.1233 | 107,397.9454 |
| I5 | 122,757.5125 | 133,685.6527 |
| I6 | 155,339.1689 | 140,537.0037 |
| I7 | 109,73353.29 | 191,101.3038 |
| I8 | 80,997.65877 | 97,607.54395 |
| I9 | 86,683.84207 | 85,500.15861 |
| IR | 27,083.49373 | 15,403.87762 |
| C1 | 2,060.088645 | 2,216.502071 |
| C2 | 2,372.907594 | 2,456.631532 |
| C3 | 1,705.281875 | 1,363.982535 |
| C4 | 2,288.671648 | 2,103.92269 |
| C5 | 1,737.126407 | 1,941.884701 |
| C6 | 2,330.533506 | 2,544.539641 |
| CR1/CR2 | 768.2952687 | 796.205777 |

TABLE 4

EIS Test Data, Batch 2

| Sample | Impedance at 1 kHz before soak ($\Omega$) | Impedance at 1 kHz after soak ($\Omega$) |
|---|---|---|
| I1 | 111,207.4125 | 117,920.724 |
| I2 | 91,710.6597 | 92,568.02844 |
| I3 | 100,553.3606 | 113,465.5162 |
| I4 | 108,649.5167 | 87,726.88188 |
| I5 | 122,961.9007 | 121,258.6925 |
| I6 | 73,091.33295 | 61,175.19394 |
| I7 | 30,181.41957 | 63,319.06496 |
| I8 | 91,944.7167 | 89,240.70176 |
| I9 | 47,613.66508 | 51,268.97149 |
| IR | 16,204.1267 | 18,989.91951 |
| C1 | 2,151.512393 | 2,018.449587 |
| C2 | 2,380.943159 | 2,537.142539 |
| C3 | 2,432.199713 | 2,406.792661 |
| C4 | 2,163.879209 | 2,467.776192 |
| C5 | 2,061.582406 | 2,600.953803 |
| C6 | 2,073.423661 | 3,225.637381 |
| CR1/CR2 | 529.245999 | 1302.300123 |

The multi-layered electronic devices disclosed herein may contain an intrafascicular portion and a cuff portion. Samples I1-I9 are intrafascicular portions. Sample IR is a reference intrafascicular portion. Samples C1-C6 are cuff portions. Sample CR1/CR2 is a reference cuff portion. Samples I1-I9 recorded an average impedance of 110,604.7 $\Omega$ (batch 1) and 88,660.42 $\Omega$ (batch 2) after the soak. Samples C1-C6 recorded an average impedance of 2,104.557 $\Omega$ (batch 1) and 2,542.792 $\Omega$ (batch 2).

Certain target tissues require an intrafascicular impedance between about 50 k$\Omega$ and 200 k$\Omega$ and a cuff impedance between about 1 k$\Omega$ and 4 k$\Omega$ Accordingly, the multi-layered electronic devices disclosed herein perform adequately for stimulating target tissues when worn and/or implanted.

Figure 11A:
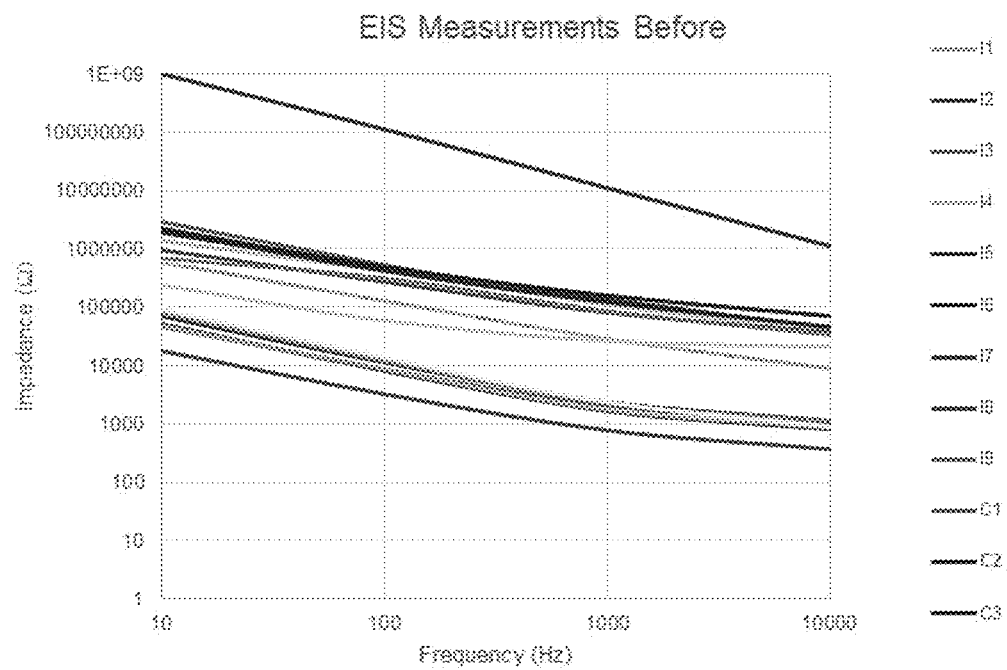
FIG. 11A is a graph of the impedance for varying frequencies of exemplary electronic devices.
Figure 11B:
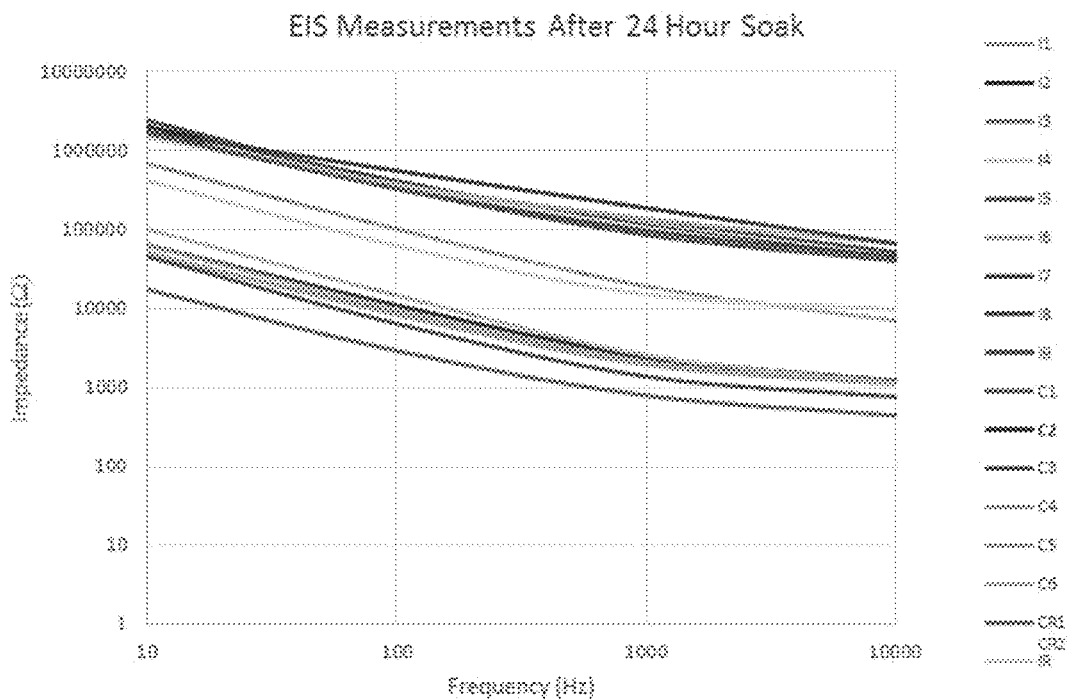
FIG. 11B is a graph of the impedance for varying frequencies of the exemplary electronic devices of FIG. 11A after soaking in a saline solution.
Figure 12A:
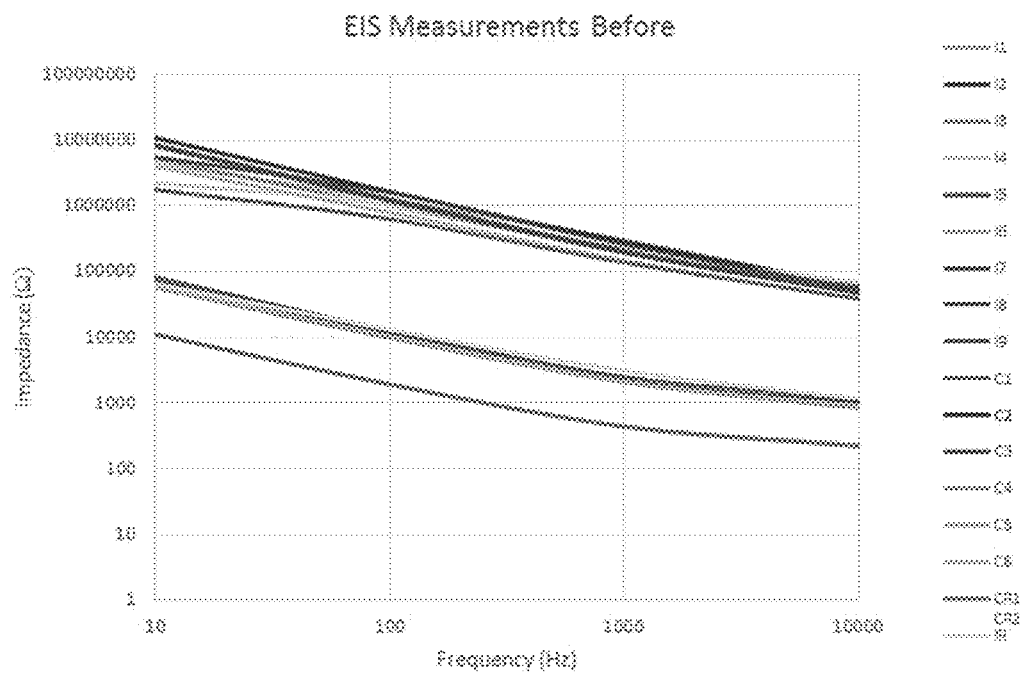
FIG. 12A is a graph of the impedance for varying frequencies of alternate exemplary electronic devices.
Figure 12B:
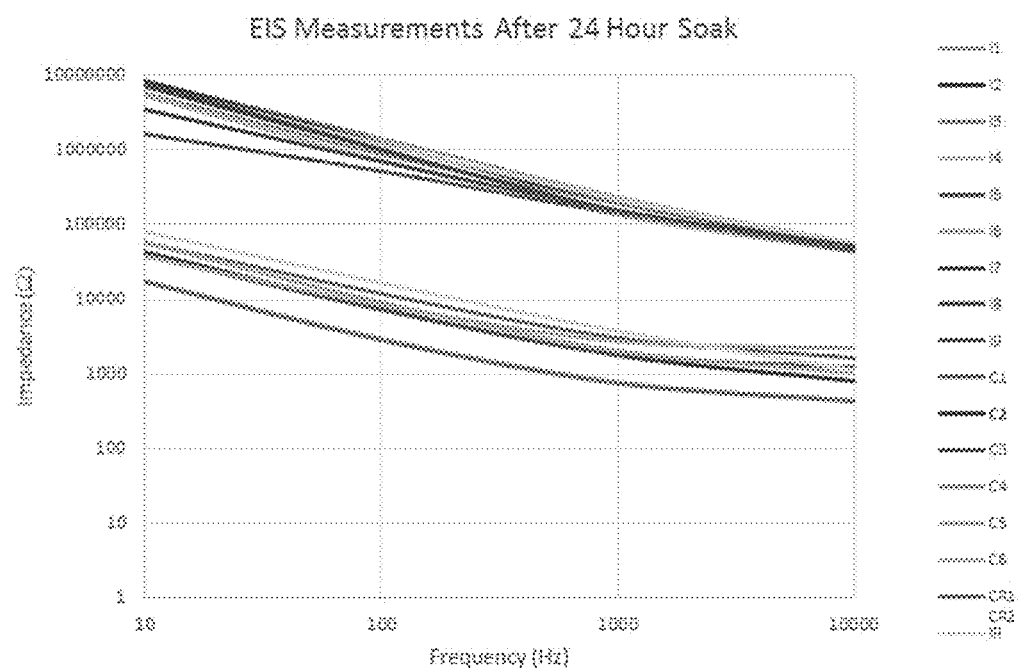
FIG. 12B is a graph of the impedance for varying frequencies of the exemplary electronic devices of FIG. 12A after soaking in a saline solution.

Additionally, as shown in the graphs presented in FIGS. 11A-11B, the recorded impedance for the samples before the soak (FIG. 11A) was generally greater than the recorded impedance for the samples after the 24-hour soak (FIG. 11B). Additionally, samples I1-I9 tended to exhibit a greater impedance than samples C1-C6. The batch 2 results shown in the graphs of FIGS. 12A-12B show a similar trend. However, in batch 2 the pre-soak and post-soak samples generally exhibited more similar impedances and the recorded impedances of the I1-I9 samples were generally more distinguishable from the recorded impedances of the C1-C6.

The aspects disclosed herein in accordance with the present invention, are not limited in their application to the details of construction and the arrangement of components set forth in the following description or illustrated in the accompanying drawings. These aspects are capable of assuming other embodiments and of being practiced or of being carried out in various ways. Examples of specific implementations are provided herein for illustrative purposes only and are not intended to be limiting. In particular, acts, components, elements, and features discussed in connection with any one or more embodiments are not intended to be excluded from a similar role in any other embodiments.

Also, the phraseology and terminology used herein is for the purpose of description and should not be regarded as limiting. Any references to examples, embodiments, components, elements or acts of the systems and methods herein referred to in the singular may also embrace embodiments including a plurality, and any references in plural to any embodiment, component, element or act herein may also embrace embodiments including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. In addition, in the event of inconsistent usages of terms between this document and documents incorporated herein by reference, the term usage in the incorporated reference is supplementary to that of this document; for irreconcilable inconsistencies, the term usage in this document controls. Moreover, titles or subtitles may be used in the specification for the convenience of a reader, which shall have no influence on the scope of the present invention.

Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure, and are intended to be within the scope of the examples discussed herein. Accordingly, the foregoing description and drawings are by way of example only.

What is claimed is:

1. An in-vivo electronic system comprising:
   at least one multi-layered electronic device comprising two or more stacked metal conducting layers, each having a trace and one or more contact pads, a dielectric layer having at least one through hole and disposed between metal conducting layers, and at least one electrical connection extending between the contact pads of metal conducting layers and through the at least one through hole of the dielectric layer;
   a satellite coupled to at least one of the at least one multi-layered electronic device; and
   a controller hub electrically connected to the at least one multi-layered electronic device via the satellite.

2. The in-vivo electronic system of claim 1, wherein the controller hub is wirelessly connectable to the satellite.

3. The in-vivo electronic system of claim 1, wherein the satellite is wirelessly connectable to the at least one multi-layered electronic device.

4. The in-vivo electronic system of claim 1, further comprising a transmission line electrically connected to the at least one multi-layered electronic device.

5. The in-vivo electronic system of any of claims 1 through 4, wherein the at least one multi-layered electronic device is configured to be one of an electrode, an antenna, and a connector.

6. The in-vivo electronic system of claim 5, wherein the at least one multi-layered electronic device is configured to be an electrode.

7. The in-vivo electronic system of claim 6, wherein the at least one multi-layered electronic device is configured to be directly secured to a subject.

8. The in-vivo electronic system of claim 5, wherein the at least one multi-layered electronic device is configured to be an antenna.

9. The in-vivo electronic system of claim 8, wherein the at least one multi-layered electronic device is arranged into a tubular structure and comprises a tubular exterior insulating layer.

10. The in-vivo electronic system of claim 1, wherein each metal conducting layer has a uniform cross-sectional geometry.

11. The in-vivo electronic system of claim 1, further comprising at least one insulating layer positioned adjacent to the at least one metal conducting layer on an exterior surface of the multi-layered electronic device, at least one support layer adjacent to the least one insulating layer, and at least one ground layer adjacent to the at least one metal conducting layer.

12. The in-vivo electronic system of claim 1, wherein at least one of the metal conducting layer and the electrical connection comprises a flexible metal foil or a thin film conductive ink.

13. The in-vivo electronic system of claim 12, wherein at least one of the metal conducting layer and the electrical connection comprises gold, platinum, or carbon nanotube ink.

14. The in-vivo electronic system of claim 1, wherein the metal conducting layer and dielectric layer together have a thickness of about 100 μm or less.

* * * * *